US007074968B2

(12) United States Patent
Sunkara et al.

(10) Patent No.: US 7,074,968 B2
(45) Date of Patent: *Jul. 11, 2006

(54) CONTINUOUS PROCESS FOR THE PREPARATION OF POLYTRIMETHYLENE ETHER GLYCOL

(75) Inventors: Hari Babu Sunkara, Hockessin, DE (US); Ernest Keith Andrew Marchildon, Kingston (CA); Howard Chung-Ho Ng, Kingston (CA); Leo E. Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/760,339

(22) Filed: Jan. 20, 2004

(65) Prior Publication Data

US 2004/0152925 A1    Aug. 5, 2004

Related U.S. Application Data

(63) Continuation of application No. 09/738,689, filed on Dec. 15, 2000, now Pat. No. 6,720,459.

(60) Provisional application No. 60/172,126, filed on Dec. 17, 1999.

(51) Int. Cl.
*C07C 41/09* (2006.01)

(52) U.S. Cl. ..................................... 568/619
(58) Field of Classification Search ................. 568/619
See application file for complete search history.

(56) References Cited

U.S. PATENT DOCUMENTS

| 2,492,955 | A |   | 1/1950  | Ballard et al.   |         |
|-----------|---|---|---------|------------------|---------|
| 2,520,733 | A |   | 8/1950  | Morris et al.    |         |
| 3,023,192 | A |   | 2/1962  | Shivers, Jr. et al. |      |
| 3,027,352 | A |   | 3/1962  | Walling et al.   |         |
| 3,192,184 | A |   | 6/1965  | Brill et al.     |         |
| 3,326,985 | A |   | 6/1967  | Mason            |         |
| 3,384,623 | A |   | 5/1968  | Inoue et al.     |         |
| 3,526,484 | A |   | 9/1970  | Kilpatrick       |         |
| 3,651,014 | A |   | 3/1972  | Witsiepe         |         |
| 3,763,109 | A |   | 10/1973 | Witsiepe         |         |
| 4,277,577 | A |   | 7/1981  | Burg et al.      |         |
| 4,482,750 | A |   | 11/1984 | Hetzel et al.    |         |
| 4,937,314 | A |   | 6/1990  | Greene           |         |
| 4,970,295 | A |   | 11/1990 | Schuchardt       |         |
| 5,070,178 | A |   | 12/1991 | Yamada           |         |
| 5,128,185 | A |   | 7/1992  | Greene           |         |
| 5,403,912 | A |   | 4/1995  | Gunatillake et al. |       |
| 5,523,451 | A |   | 6/1996  | Rechner et al.   |         |
| 5,659,089 | A |   | 8/1997  | Cai et al.       |         |
| 5,674,974 | A |   | 10/1997 | Brearley et al.  |         |
| 5,677,415 | A |   | 10/1997 | Bhatia           |         |
| 5,731,453 | A | * | 3/1998  | Nishihira et al. | 558/274 |
| 5,814,282 | A |   | 9/1998  | Lohe et al.      |         |
| 6,187,898 | B1| * | 2/2001  | Wagner et al.    | 528/328 |
| 6,235,948 | B1|   | 5/2001  | Sunkara et al.   |         |
| 6,720,459 | B1| * | 4/2004  | Sunkara et al.   | 568/619 |
| 2002/0007043 | A1 | * | 1/2002 | Sunkara et al.  | 528/396 |

FOREIGN PATENT DOCUMENTS

| DE | 42 36 039    |   | 4/1994 |
|----|--------------|---|--------|
| WO | WO 94/09055  |   | 4/1994 |
| WO | WO 96/13540  |   | 5/1996 |
| WO | WO 98/37123  | * | 8/1998 |
| WO | WO 99/01496  |   | 1/1999 |
| WO | WO 00/10953  |   | 3/2000 |

OTHER PUBLICATIONS

International Search Report from PCT/US 00/34203.
English Abstract of DE 42 36 039.
U.S. Appl. No. 09/638,356, filed Aug. 15, 2000.
U.S. Appl. No. 09/727,792, filed Dec. 1, 2000.
S.V. Conjeevaram, R.S. Benson & D.J. Lyman, "Block Copolyurethanes Based on Polyoxytrimethylene Glycols", Journal of Polymer Science: Polymer Chemistry Edition, 1985, pp. 429-444, vol. 23.
Cesar Carlos Gonzalez, Antonio Bello, Jose Manuel Perena, "Oligomerization of Oxetane and Synthesis of Polyterephthalates Derived from 1,3-Propanediol and 3,3'-Oxydipropanol", Makromol. Chem. 190, No. 6, Jun. 1989, pp. 1217-1224.
Pathiraja A. Gunatillake, Gordon F. Meijs, Ronald C. Chatelier, Donna M. McIntosh & Ezio Rizzardo, "Synthesis and Characterization of Hydroxy-Terminated Poly(Alkylene Oxides) by Condensation Polymerization of Diols", Polymer International, 1992, pp. 275-283, vol. 27, No. 3.
Simon J. McCarthy, Gordon F. Meijs, Pathiraja Gunatillake, "Synthesis, Characterization, and Stability of Poly[(alkylene oxide) ester] Thermoplastic Elastomers", 1997; pp. 1319-1332.
M. Younus Qureshi & Matthias Ochel, "Synthesis and Characterization of High Molecular Weight Poly(Trimethylene Oxide)", Pergamon, 1996, pp. 691-693, vol. 32, No. 6.
Milton J. Rhoad & Paul J. Flory, "The Synthesis of Polymeric Ethers", Contribution No. 169 from The Goodyear Tire and Rubber Co., Research Laboratory, May 1950; pp. 2216-2219, vol. 72.

* cited by examiner

*Primary Examiner*—Rosalynd Keys
(74) *Attorney, Agent, or Firm*—Mark D. Kuller; Bart E. Lerman

(57) ABSTRACT

The invention is a continuous process for the preparation of polytrimethylene ether glycol from 1,3-propanediol reactant. In addition, the invention is directed to a continuous multi-stage process comprising reacting at least one reactant in a liquid phase in an up-flow column reactor, and forming a gas or vapor phase by-product wherein the gas or vapor phase by-product is continuously removed at the top and at least one intermediate stage.

57 Claims, 7 Drawing Sheets

US 7,074,968 B2

CONTINUOUS PROCESS FOR THE PREPARATION OF POLYTRIMETHYLENE ETHER GLYCOL

This application is a continuation of patent application Ser. No. 09/738,689, filed Dec. 15, 2000 and issued on Apr. 13, 2004 as U.S. Pat. No. 6,720,459, which claims priority from U.S. provisional patent application Ser. No. 60/172,126, filed Dec. 17, 1999, which are incorporated herein by reference.

FIELD OF THE INVENTION

This invention concerns a process and reactor for the preparation of polytrimethylene ether glycol from 1,3-propanediol reactant. In addition, the invention is directed to a continuous multi-stage process in an upflow column reactor involving forming a gas or vapor phase by-product.

TECHNICAL BACKGROUND OF THE INVENTION

Known polyalkylene ether glycols include polyethylene glycol, poly-1,2- and 1,3-propylene ether glycol, polytetramethylene ether glycol, polyhexamethylene ether glycol and copolymers thereof. They have been used widely as lubricants or as starting materials for preparing lubricants used in the molding of rubbers and in the treatment of fibers, ceramics and metals. They have also been used as starting materials for preparing cosmetics and medicines, as starting materials or additives for water-based paints, paper coatings, adhesives, cellophane, printing inks, abrasives and surfactants and as starting materials for preparing resins, such as alkyd resins. They have also been used as soft, flexible segments in the preparation of copolymers and segmented copolymers such as polyurethanes, thermoplastic polyesters and unsaturated polyester resins. Examples of commercially important polyether glycols include polyethylene glycol, poly(1,2-propylene glycol), ethylene oxide/propylene oxide copolyols, and polytetramethylene ether glycol.

Among the polyether glycols, the most widely used polyether glycol is poly(1,2-propylene glycol) (PPG) because of its low cost. This polymer is non-crystalline, liquid at room temperature and hence easy to handle. However, PPG has secondary hydroxyl end groups and it contains high percentages of terminal unsaturation.

Polyoxytrimethylene glycol or polytrimethylene ether glycol or poly(1,3-propylene glycol) can be derived either from 1,3-propanediol or from oxetane. These polytrimethylene ether glycols have primary hydroxyl groups and have low melting points and are highly flexible.

U.S. Pat. No. 2,520,733, which is incorporated herein by reference, discloses polymers and copolymers of trimethylene glycol and a process for the preparation of these polymers from trimethylene glycol in the presence of a dehydration catalyst such as iodine, inorganic acids (e.g., sulfuric acid) and organic acids. The trimethylene glycol derived polymers disclosed in this patent are dark brown or black in color. The color can be improved to a light yellow color by treatment processes disclosed therein. Polymers of molecular weight from about 100 to about 10,000 are mentioned; however, there is a preference for molecular weights of 200–1,500 and the highest molecular weight shown in the examples is 1096.

U.S. Pat. No. 3,326,985, which is incorporated herein by reference, discloses a process for forming a polytrimethylene glycol having an average molecular weight of 1,200–1,400. First, polytrimethylene glycol which has an average molecular weight of about 900 is formed using hydriodic acid. This is followed by an after treatment which comprises vacuum stripping the polyglycol at a temperature in the range of 220–240° C. and at a pressure of 1–8 mm Hg in a current of nitrogen from 1–6 hours. The product is stated to be useful in preparing polyurethane elastomers. There is also presented a comparative example directed to producing polytrimethylene glycol with a molecular weight of 1,500.

U.S. Pat. No. 5,403,912, which is incorporated herein by reference, disclosed a process for the polymerization of polyhydroxy compounds, including alkanediols having from 2–20 carbon atoms, in the presence of an acid resin catalyst at temperatures of from 130–220° C. Molecular weights of from 150 to 10,000 are mentioned. A copolymer of 1,10-decanediol and 1,3-propanediol having a number average molecular weight of 2050 was exemplified.

Preparation of ester terminated polyethers and hydroxy terminated polyethers from oxetanes and or mixtures of oxetanes and oxolanes by ring opening polymerization is disclosed U.S. Pat. No. 4,970,295, which is incorporated herein by reference. The resulting polyethers are stated to have molecular weights in the range of 250–10,000, preferably 500–4,000. Synthesis of polyoxytrimethylene glycols from oxetane is also described in S. V. Conjeevaram, et al., Journal of Polymer Science: Polymer Chemistry Ed., Vol. 23, pp 429–44 (1985), which is incorporated herein by reference.

It is desirable to prepare said polyether glycol from readily available materials, not, for example, from the commercially unavailable oxetane. The polytrimethylene ether glycols heretofore obtained from the polycondensation of 1,3-propanediol are of low molecular weight, are highly discolored and/or require long reaction times. In addition, heretofore all process for preparing polytrimethylene ether glycol from 1,3-propanediol reactant have been batch processes. Therefore, a continuous process that produces polytrimethylene ether glycol in high yield, preferably with little or no color, and desired molecular weight, has been sought.

SUMMARY OF THE INVENTION

This invention is directed to a process of making polytrimethylene ether glycol comprising:
(a) providing 1,3-propanediol reactant and polycondensation catalyst; and
(b) continuously polycondensing the 1,3-propanediol reactant to polytrimethylene ether glycol.

Preferably, the polycondensing is carried out in two or more reaction stages.

The polycondensing is preferably carried out at a temperature greater than 150° C., more preferably greater than 160° C., and most preferably greater than 180° C., and is preferably carried out at a temperature less than 250° C., more preferably less than 220° C., and most preferably less than 210° C.

The polycondensation is preferably carried out at a pressure of less than one atmosphere, more preferably less than 500 mm Hg, and even more preferably less than 250 mm Hg. While still lower pressures, for example, even as low as 1 mm Hg can be used, especially for small scale operation, for larger scale, pressure is at least 20 mm Hg, preferably at least 50 mm Hg. On a commercial scale, the polycondensation pressure will normally be between 50 and 250 mm Hg.

In one preferred embodiment, the 1,3-propanediol reactant is selected from the group consisting of 1,3-propanediol and/or dimer and trimer of 1,3-propanediol and mixtures thereof. In another preferred embodiment, the 1,3-propanediol reactant is selected from the group consisting of the 1,3-propanediol or the mixture containing at least 90 weight % of 1,3-propanediol. In yet another preferred embodiment, the 1,3-propanediol reactant is the 1,3-propanediol.

In one preferred embodiment, the catalyst is homogeneous. Preferably, the catalyst is selected from the group consisting of a Lewis Acid, a Bronsted Acid, a super acid, and mixtures thereof. More preferably, the catalyst is selected from the group consisting of inorganic acids, organic sulfonic acids, heteropolyacids, and metal salts thereof. Even more preferably the catalyst is selected from the group consisting of sulfuric acid, fluorosulfonic acid, phosphorus acid, p-toluenesulfonic acid, benzenesulfonic acid, phosphotungstic acid, phosphomolybdic acid, trifluoromethanesulfonic acid, 1,1,2,2-tetrafluoro-ethanesulfonic acid, 1,1,1,2,3,3-hexafluoropropanesulfonic acid, bismuth triflate, yttrium triflate, ytterbium triflate, neodymium triflate, lanthanum triflate, scandium triflate and zirconium triflate. The most preferred catalyst is sulfuric acid.

In another preferred embodiment, the catalyst is heterogeneous. Preferably, the catalyst is selected from the group consisting of zeolites, fluorinated alumina, acid-treated silica, acid-treated silica-alumina, heteropolyacids and heteropolyacids supported on zirconia, titania, alumina and/or silica.

In a preferred embodiment, the polycondensation is carried out in a reactor equipped with a heat source located within the reaction medium.

In one preferred embodiment, the polycondensation is carried out in an upflow co-current column reactor and the 1,3-propanediol reactant and polytrimethylene ether glycol flow upward co-currently with the flow of gases and vapors. Preferably, the reactor has two or more stages, more preferably 3–30 stages, even more preferably 4–20 stages, and most preferably 8–15 stages.

In one preferred embodiment, the 1,3-propanediol reactant is fed at multiple locations to the reactor. In addition, an inert gas is preferably added to the reactor at one or more stages. Further, preferably at least some amount of steam (water vapor) that is generated as a by-product of the reaction is removed from the reactor at least one intermediate stage.

In another preferred embodiment, the polycondensation is carried out in a counter current vertical reactor wherein and the 1,3-propanediol reactant and polytrimethylene ether glycol flow in a manner counter-current to the flow of gases and vapors. Preferably, the reactor has two or more stages, more preferably 3–30 stages, even more preferably 4–20 stages, and most preferably 8–15 stages. Preferably, the 1,3-propanediol reactant is fed at the top of the reactor. Even more preferably, the 1,3-propanediol reactant is fed at multiple locations to the reactor.

In yet another preferred embodiment, the polycondensation is first carried out in at least one prepolymerizer reactor and then continued in a column reactor. The 1,3-propanediol reactant preferably comprises 90 weight % or more 1,3-propanediol. Preferably, in the prepolymerizer reactor the 1,3-propanediol is polymerized with the catalyst to a degree of polymerization of at least 5. More preferably, the 1,3-propanediol is polymerized with the catalyst to a degree of polymerization of at least 10 and the column reactor comprises 3–30 stages. Preferably, in the at least one prepolymerizer reactor the 1,3-propanediol is polymerized with the catalyst to a degree of polymerization of at least 20. In the most preferred embodiment, the at least one prepolymerizer reactor the 1,3-propanediol is polymerized with the catalyst to a degree of polymerization of 5–10. Most preferably, the at least one prepolymerizer reactor is a well-mixed tank reactor. Most preferably, steam generated in the at least one prepolymerizer reactor is removed and the product of the at least one prepolymerizer is fed to the column reactor.

Preferably, an inert gas is fed to the column reactor.

This invention is also directed to a continuous multi-stage process comprising reacting at least one reactant in a liquid phase in an upflow column reactor, and forming a gas or vapor phase by-product wherein the gas or vapor phase by-product is continuously removed at the top and at least one intermediate stage. Preferably, the gas or vapor phase by-product is water.

DETAILED DESCRIPTION OF THE INVENTION

Figure 1:
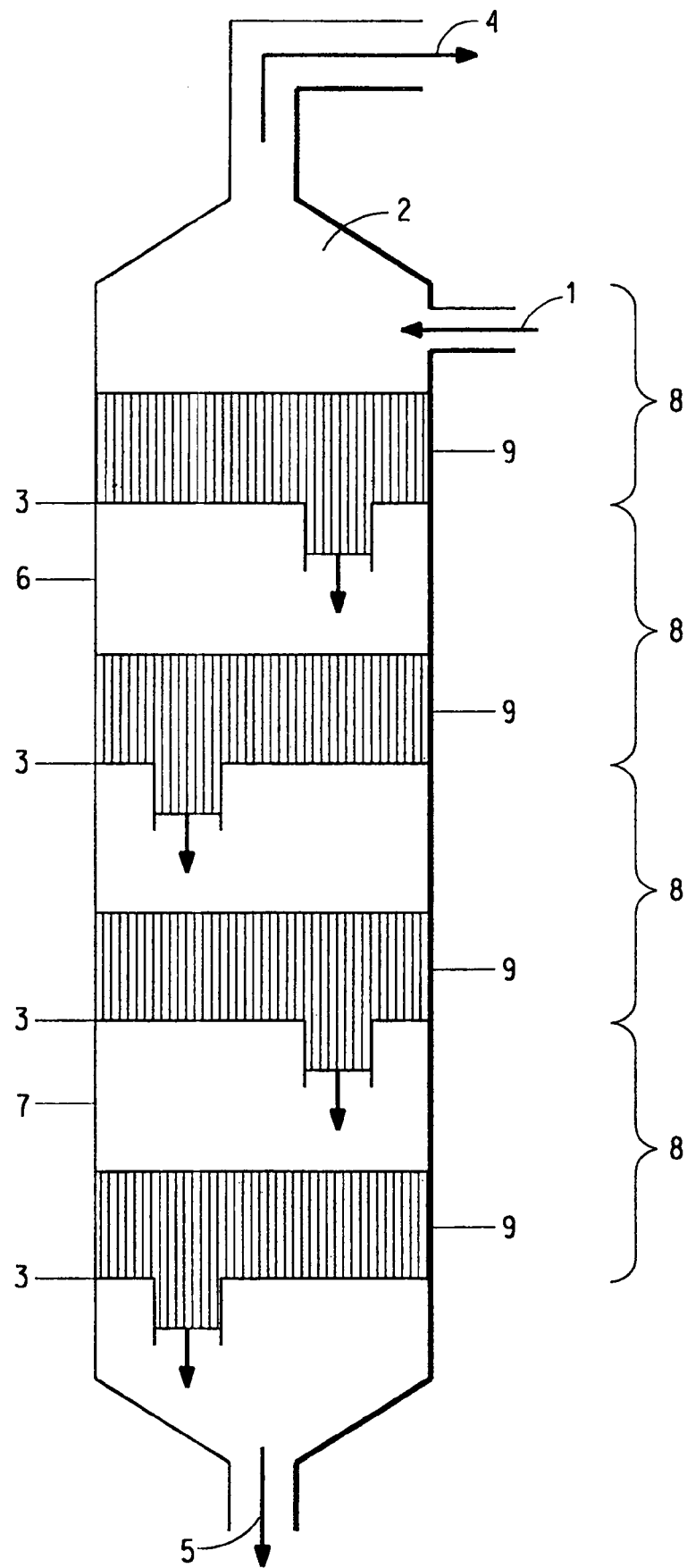
FIG. 1 illustrates diagrammatically a multistage reactor. The reactor is divided into four discrete stages using barriers between stages, which barriers allow separate passages for vapor and liquid flows from stage to stage.

The invention is a method for manufacture of polytrimethylene ether glycol, a polyether, continuously from the dehydration/condensation polymerization of 1,3-propanediol reactant using a polycondensation catalyst.

Herein, "1,3-propanediol reactant" means 1,3-propanediol and/or oligomers or prepolymers of 1,3-propanediol having a degree of polymerization of 2–9 and mixtures thereof; "oligomer" is used to refer to dimer and trimer of 1,3-propanediol; and "prepolymer" is used to refer to 1,3-propanediol based compounds having a degree of polymerization of 4–9. Herein, when referring to "polytrimethylene ether glycol" or copolymer, reference is made to polymers or copolymers having a Mn of 1000 or more.

Polytrimethylene ether glycol is sometimes referred to as "polyoxytrimethylene glycol" or "3G polyol", and 1,3-propanediol is sometimes referred to as "trimethylene glycol" or "3G". For convenience and ease of reading, 1,3-propanediol, 3G, is sometimes used to refer to 1,3-propanediol, its oligomers, prepolymers or mixtures thereof in discussing the invention in the specification (e.g., with explaining the Figures), but not in the Examples.

The process of the invention can be operated at pressures ranging from above atmospheric, atmospheric or below atmospheric pressure. However, to achieve a number average molecular weight of greater than 1000, typically the polycondensation (or at least the later portion of polycondensation) is carried out at a pressure of less than one atmosphere, preferably less than 500 mm Hg, more preferably at a pressure less than 250 mm Hg. While still lower pressures, for example, even as low as 1 mm Hg can be used, especially for small scale operation, for larger scale, pressure is at least 20 mm Hg, preferably at least 50 mm Hg. Most suitable pressures are in the range of 50–250 mm Hg. A pressure of 100 mm Hg can be used to produce a polytrimethylene ether glycol of molecular weight greater than 1500.

Low pressure processes are described in U.S. patent application Ser. No. 6,977,291, filed concurrently herewith, and the provisional patent application 60/172,264, filed Dec. 17, 1999, both of which are incorporated herein by reference.

Temperature of the process is preferably controlled to achieve the goals of the invention, that is, high yields of desired molecular weight and a minimum of color formation. Temperature range is generally greater than 150° C. to achieve desired reaction rates, preferably greater than 160° C., and more preferably greater than 180° C. Temperature is generally less than 250° C., preferably less than 220° C., and more preferably less than 210° C. to minimize color. If the equipment is suitable, the temperature may be increased through the course of the reaction.

A suitable control system can consist of simply ensuring that all material experiences the same sequence of temperature and pressure as it passes through the reactor or it may employ an automatic control mechanism where one or more operating conditions of the reactor are continually adjusted to maintain a more or less constant value of some measured property (e.g., viscosity) of the polymer which is related to the molecular weight.

The process of this invention is not limited by reactor configuration. However a successful manufacturing process for polytrimethylene ether glycol should provide the product within a desired time and under conditions to achieve the average molecular weight for end use applications and to limit the production of undesired chemical species that would make the product unsuitable for end use applications or that would require costly measures to remove. The process should further provide for separation of water, which is produced as a by-product, from the polymeric product.

Numerous reactor configurations for continuous processes are known in the chemical process industries and could be used for the manufacture of polytrimethylene glycol. The reactor can be constructed of any material sufficient to withstand corrosion when contacted with strong acid catalysts. Glass and Hastelloy® metal alloy are preferred reactor materials. Examples of reactors useful in the process of this invention include the following:

(1) Single vessels with a substantial degree of back-mixing, with or without mechanical agitation, such that the dwell time within the vessel of an identified portion of entering material is more or less random. The vessel should include a heater to convert the water by-product into steam, a control of liquid level such that a well-defined vapor space was maintained, and a point of exit of the vapor separate from the point of exit of the liquid.

(2) Sequences of back-mixed vessels, with the reaction mixture from one vessel continuously or intermittently constituting the feed for the next. The steam by-product may also be conveyed from each vessel to the next or may be discharged to a separate receptacle.

(3) Combinations of vessels which continuously exchange material with one another at a rate which is high enough relative to the main flow of material into and out of the combination of vessels that the combination acts as a single fully-back-mixed or partially-back-mixed vessel.

(4) Horizontal or vertical vessels of large ratio of length to cross-sectional linear dimension (i.e., pipes and columns) through which the reacting material flows and in which identified portions of the material pass any point along the length in approximately the same order as at any other point (commonly known as "plug flow"). Heat should be supplied along the length to conduct the polycondensation and to convert the water by-product into steam. The steam may flow in the same direction ("co-current") as the reaction mixture or in the opposite direction ("countercurrent"). At one end or the other or at some intermediate point in the vessel a point of vapor release must be provided, where vapor can leave and carry only a negligible amount of liquid with itself. The pipe or column may be provided with one or more partial barriers which allow passage of the liquid and steam in the desired directions but which largely prevent back-flow of liquid.

(5) Combinations of back-mixed vessels and pipes or columns, generally in sequence.

(6) Vessels incorporating large vertical surfaces, down which the reaction mixture flows and reacts.

(7) Vessels incorporating large moving horizontal surfaces, on which the reacting material is conveyed and reacts.

(8) Hybrid batch-continuous systems where part of the process is carried out in each mode. Typically the feed material is prepared in batches and fed continuously to a continuous reactor, or the product of the continuous reactor is further processed as individual batches.

In the process of this invention, the monomer, along with any optional comonomers (as discussed below) is fed to the reactor. The condensate water, any unreacted monomer and any volatile by-products are vaporized and exit from the reactor for optional subsequent separation and recycle of reactive components. The unreacted monomers or low molecular weight oligomers are preferably recycled back to the reactor, continuously, for the sake of process economics and environmental concerns.

While a number of different reactor configurations can be used for the continuous process of the present invention, preferably the reactor is a column reactor, more preferably a vertical column reactor. By vertical, it is meant substantially vertical, in that there can be tilt or angle to the reactor.

Both co-current flow and counter-current flow reactors are useful in the process of this invention. A co-current reactor may be further described as an upflow co-current reactor, which means monomer enters the bottom of the reactor and product is removed from the top. Counter current reactors are also useful, wherein monomer enters at the top and product is removed from the bottom of the reactor. In one embodiment, the reactor is an upflow, co-current reactor.

Column reactors useful in this invention can either be in single stage or multiple stage configuration. Preferably the column reactor has multiple stages, for example, provided by means of partial barriers, in which the reaction mixture (monomer, oligomers, polymer, dissolved water) flow in one direction. If the reactor is cocurrent, the vapors (water, inert gas vaporized monomer) flow in the same direction, also without flow reversal. If the reactor is countercurrent, the barrier are designed to allow vapor and liquid to flow in opposite directions without mutual interference. In all cases, separation of steam and reaction mixture take place at the top of the reactor.

While the process of this reaction can be performed in a single stage continuous reactor, preferably, there are at least two stages, more preferably 3 or more stages, still more preferably 4 or more stages, and most preferred 8 or more stage. Preferably, there are up to 30 stages, still more preferably up to 20 stages, and most preferably up to 15 stages.

The column type of reactor has the advantages of
(1) low back-flow of reaction mixture from stage to stage using standard engineering methods to specify the open area of the partial barriers,
(2) opportunity in the upper stages for the re-condensation of monomer that becomes vaporized in the lower stages where its concentration is high,
(3) good agitation in all stages above the lowest, due to the passage of steam bubbles generated below,
(4) removal of volatile impurities by steam stripping,
(5) effective use of injected nitrogen, which is forced to pass through all stages above the place where it is injected, and
(6) ease of installation of stationary solid heterogeneous catalyst.

A key to the present invention is that efficient heat transfer from the column to the reactant(s) takes place. This can be accomplished by designing the column wall configuration or by placing good heat transfer materials such as glass beads of optimum surface to volume ratio, in each stage of the column. Alternatively this can be accomplished by providing a heat source located within the reaction medium. The heat source is preferably an internal replaceable heat source, preferably with non-fluid heating media. By replaceable, it is meant that the heat source can be replaced without the need to shut down the equipment to remove if a heater burns out. For example, there can be an internal heater located centrally to the column reactor. Other heat sources useful for this invention are well known.

As stated previously, preferably the process is operated at less than one atmosphere pressure. Sub-atmospheric pressure facilitates removal of the by-product water from the reaction mixture and also facilitates the removal of volatile impurities. To assist in removing water from the mixture, an inert gas (i.e., a gas which does not react with or appreciably dissolve in the reaction mixture, e.g., nitrogen) may be injected into the vessel at some point along its length. To further assist in removing water from the reaction mixture, an intermediate point of steam removal may be provided along the length of the vessel.

In the attached Figures, the catalysts are shown as rectangular boxes for simplicity. This is used to indicate that catalyst is present in the stage depicted, and the catalyst form, shape, size, etc., will vary.

A countercurrent embodiment of the invention is diagrammatically illustrated in FIG. 1. FIG. 1 illustrates the optional placement of solid supported catalyst (9) in each of four reaction stages (8). In the presence of the solid supported catalyst, monomer is introduced at (1). In the absence of the solid supported catalyst, 1,3-propanediol and catalyst are introduced to the first stage of the reactor either separately (catalyst introduced at (2)) or with the catalyst premixed with the 1,3-propane diol stream (1). The process stream moves down through the stages which are separated by barriers (3). The barriers are designed such that the reaction mixture flows downwardly while volatiles are allowed to flow upwardly, ultimately exiting the reactor at (4). Polytrimethylene ether glycol product exits the column at (5). Temperature may be uniform throughout the column, or may differ at different stages, for instance at (6) and (7).

Figure 2:
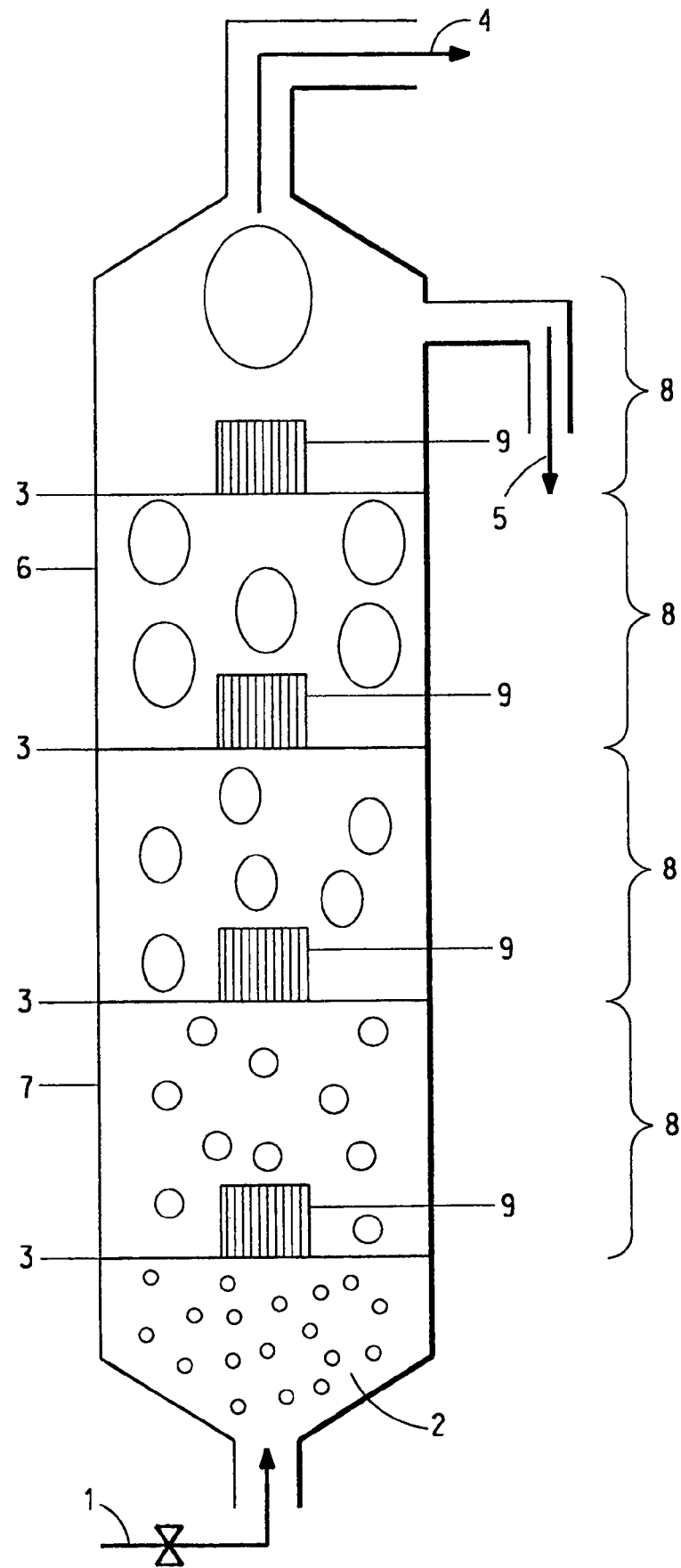
FIG. 2 illustrates diagrammatically a co-current, upflow, multistage reactor.

An upflow reactor embodiment is presented in FIG. 2. The embodiment of FIG. 2 again illustrates the optional placement of solid supported catalyst (9) in each of four reaction stages (8). In the presence of the solid supported catalyst, monomer is introduced at (1). In the absence of the solid supported catalyst, 1,3-propanediol and catalyst are introduced to the first stage of the reactor either separately (catalyst introduced at (2)) or with the catalyst premixed with the 1,3-propane diol stream (1). The process stream moves up through the stages which are separated by barriers (3). These barriers are designed such that the reaction mixture flows upwardly while volatiles are also allowed to flow upwardly, ultimately exiting the reactor at (4). Polytrimethylene ether glycol product exits the column at (5). Temperature may be uniform throughout the column, or may differ at different stages, for instance at (6) and (7).

Figure 3:
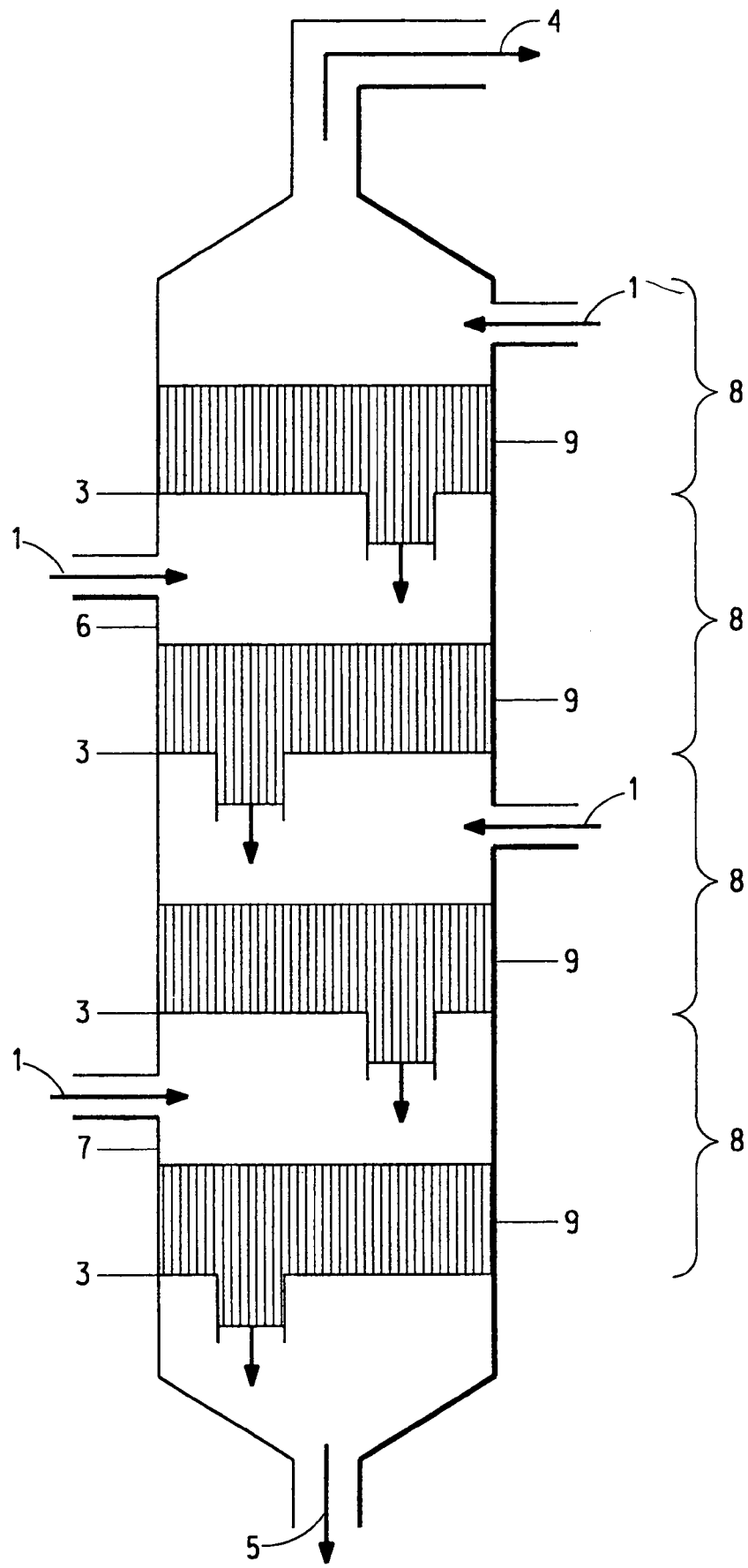
FIG. 3 illustrates diagrammatically a multistage reactor with multiple feed points.

A multi-feed reactor embodiment is presented in FIG. 3. FIG. 3 also illustrates the optional placement of solid supported catalyst (9) in each of four reaction stages (8). In the presence of the solid supported catalyst, monomer is introduced at individual feed points (1) corresponding to some or all of the reactor stages. In the absence of the solid supported catalyst, 1,3-propanediol and catalyst are introduced to each stage of the reactor either separately or with the catalyst premixed with the 1,3-propane diol stream at one or more of each (1) feed point. The process stream moves down through the stages which are separated by barriers (3). The barriers are designed such that the reaction mixture flows downwardly while volatiles are allowed to flow upwardly, ultimately exiting the reactor at (4). Polytrimethylene ether glycol product exits the column at (5). Temperature may be uniform throughout the column, or may differ at different stages, for instance at (6) and (7).

Figure 4:
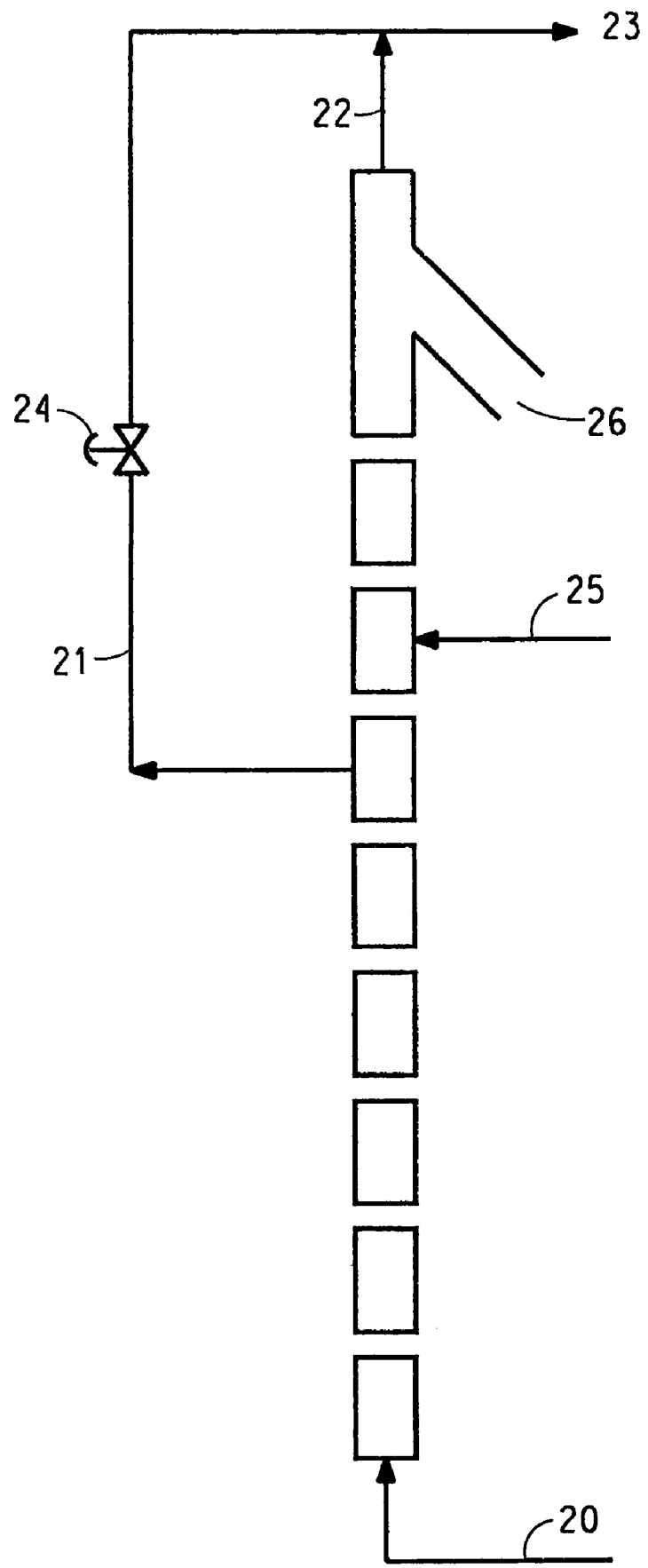
FIG. 4 illustrates diagrammatically a multi-stage column reactor with capability for removal of vapor at an intermediate stage.

FIG. 4 illustrates diagrammatically a multi-stage cocurrent, upflow column reactor with the capability to remove steam, which is the condensate water vapor generated as a product of the reaction, at a particular point. As there may also be monomer present in the lower reaction stages, this step is preferred not to take place in those stages. In this figure, monomer, 1,3-propanediol is added at the bottom (20) of the reactor. A side-stream comprised of water vapor is removed at (21), which combines with water from the top of the reactor (22) for subsequent treatment (23). A valve (24) can be used to control the removal of the water vapor. Further illustrated in this figure is addition of an inert gas at (25), to the reactor beyond where water was removed. The inert gas can be any gas that is chemically inert and not substantially soluble in the reaction medium. Nitrogen is the preferred inert gas. Polymer product exits the reactor at (26).

Figure 5A:
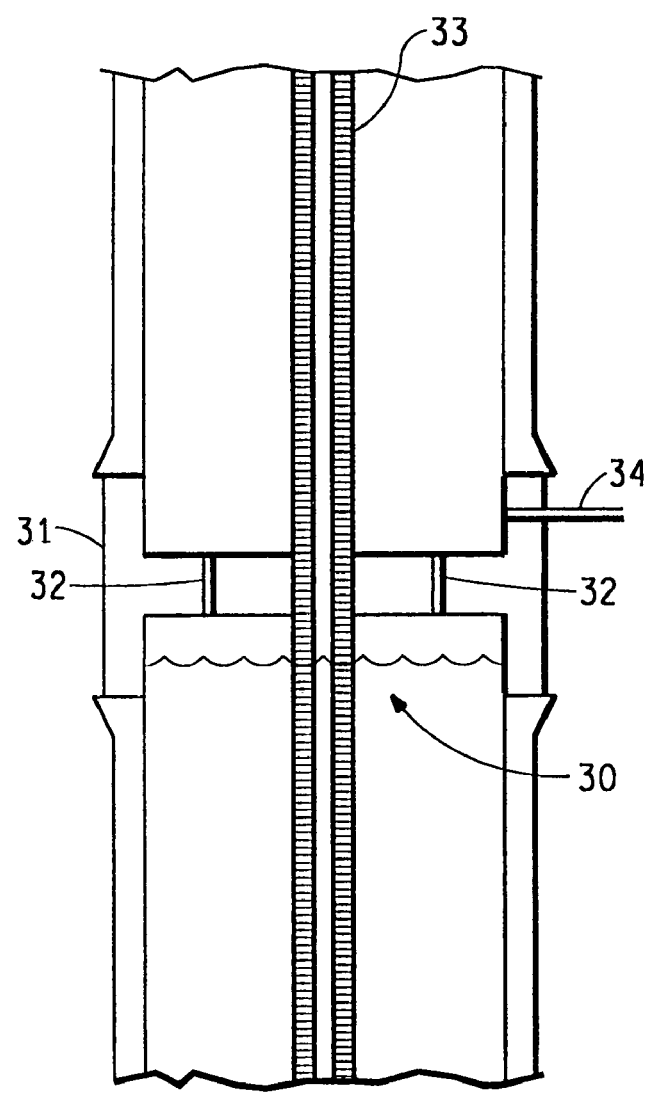
FIGS. 5a and 5b illustrate an internal column section, which provides passage of liquid and vapor between stages, and a view of a barrier separating the stages.
Figure 5B:
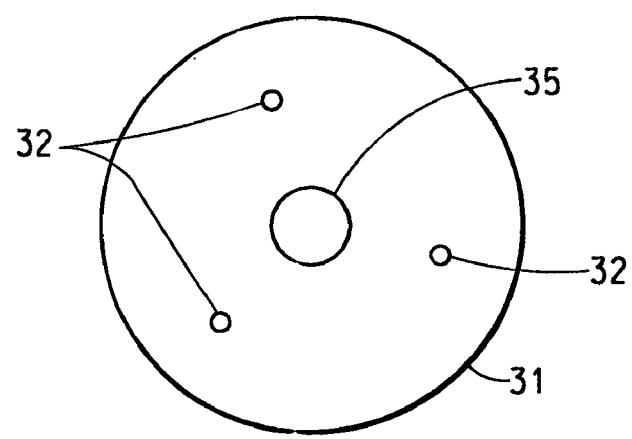

FIGS. 5a and 5b illustrate a view of an internal section of the reactor of FIG. 4. The liquid level fills the reactor stage at (30) and the reaction mixture plus gas and vapors pass through openings (32) in the barrier (31) between the stages. A side opening (34) in the barrier (31) allows for introduction of inert gas. A centrally located heater (33) is shown. The overhead view of a barrier (31) shows a large central opening (35) for the heater and three additional openings (32) through which the reaction mixture plus gas and vapors pass.

Figure 6A:
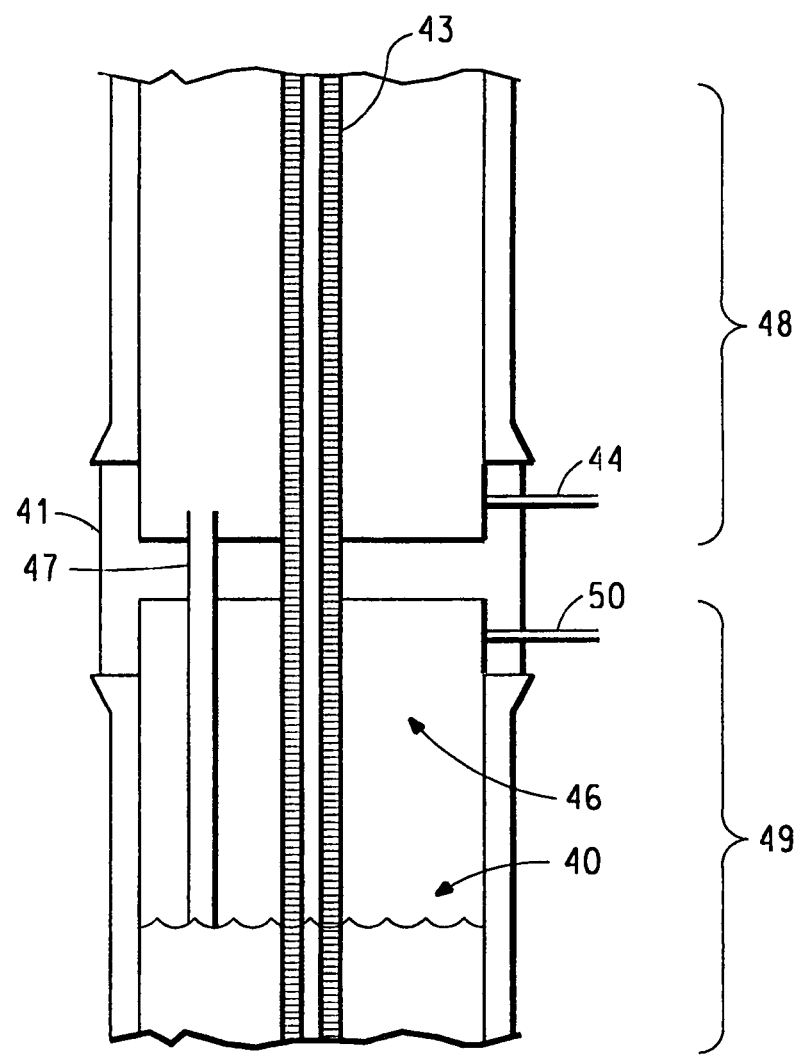
FIGS. 6a and 6b illustrate an internal column section, which provides passage of liquid between stages, removal of vapor and addition of inert gas.
Figure 6B:
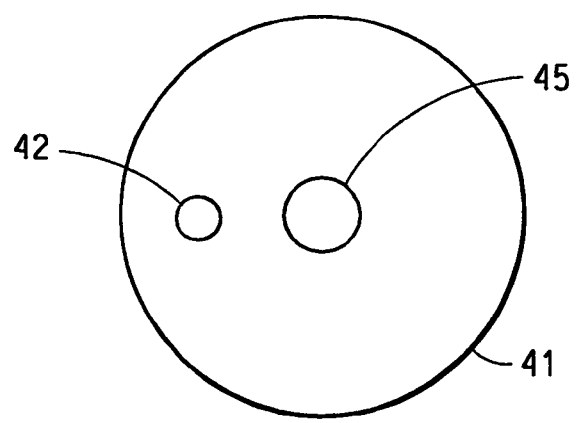

FIGS. 6a and 6b illustrate an alternative internal section of the reactor of FIG. 4. In this section, there is a liquid level (40) and a vapor space (46). A dipleg (47) drops from an upper stage (48) to below the liquid level (40) in a lower stage (49) to create a path for substantially liquid from the reaction mixture to pass from the lower stage (49) to the upper stage (48). There is also provided an opening (50) on the side of barrier (41) to provide for removal of vapor from the vapor space (46). The vapor comprises water vapor and volatiles in the reaction mixture. There is a side opening (44) in barrier (41) to allow for introduction of an inert gas. A centrally located heater (43) is shown. The overhead view of the barrier (41) shows a large central opening (45) for the heater and one additional opening (42), which is connected to dipleg (47) for liquid to pass from lower stage (49) to upper stage (48).

Figure 7:
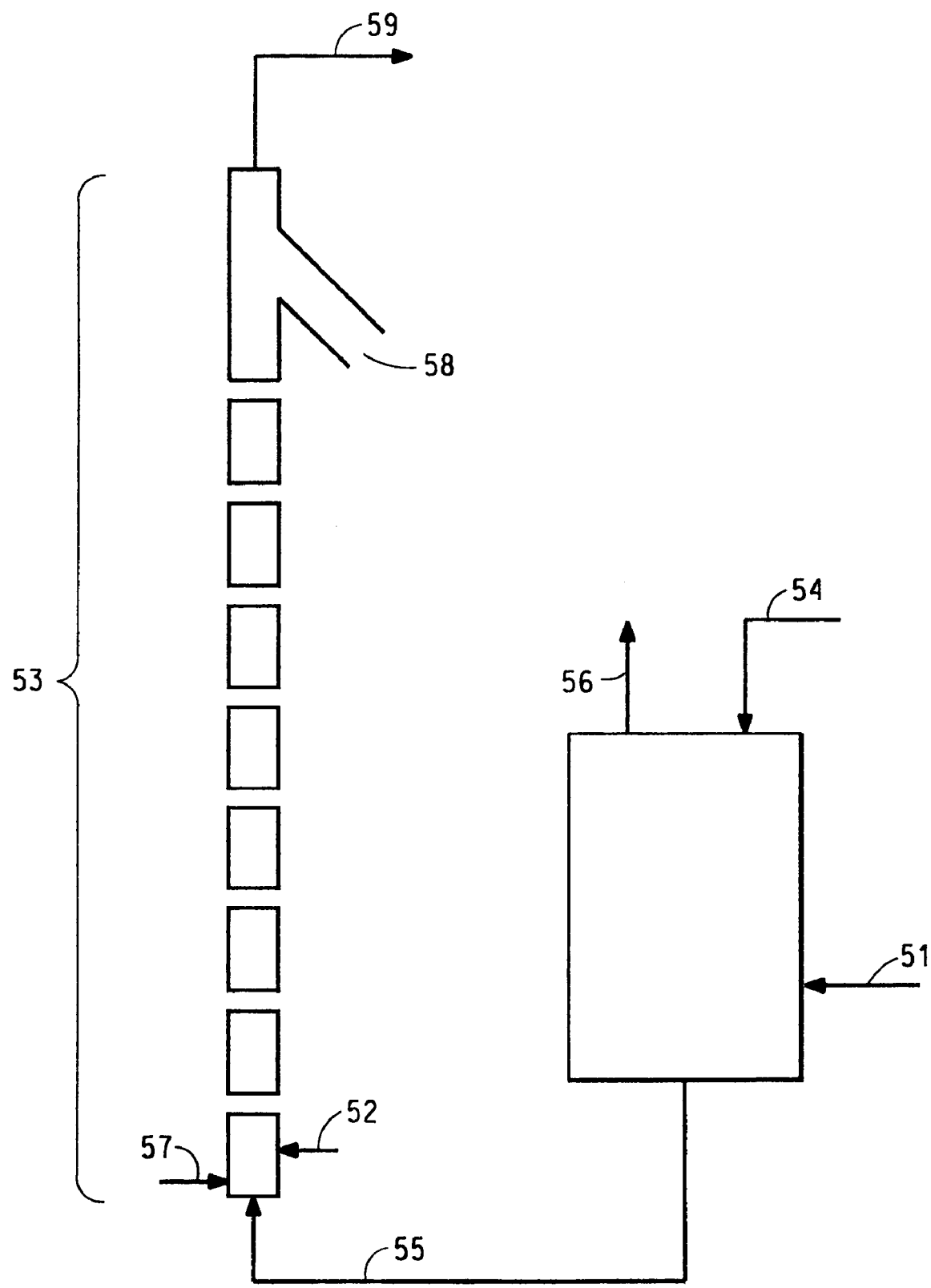
FIG. 7 illustrates diagrammatically a reactor system comprised of two separate reactors, one for polymerizing 1,3-propanediol to an intermediate molecular weight greater than that of the starting material and less than that of the desired final product, for instance a degree of polymerization of 2 to 20, preferably 5–10, and a second reactor to polymerize the intermediate to higher molecular weight.

FIG. 7 illustrates an alternative embodiment wherein a large part of the reaction is carried out in a non-columnar reactor (51) comprising one or more stages and the reaction mixture is continuously conveyed from this vessel into the lowest stage (52) of a multi-stage co-current upflow column reactor (53). Monomer, 1,3-propanediol (54) is fed into vessel (51), then fed via piping (55) into stage (52). Steam produced in the reaction is vented from vessel (51) at (56). An inert gas is shown added to stage (52) at (57). Polymer product is removed at (58) and the reaction vapors are vented at (59). This arrangement reserves the column for the final portion of the reaction where the use of multiple sequential stages is important for efficiency of reaction. For a given rate of production the size of the column can be reduced, with much of the reaction being carried out in a less expensive first vessel. The two vessels may be operated under different pressures, with the first vessel being preferably operated at a pressure closer to atmospheric than the column. The column is preferably operated under vacuum. (This arrangement can also be used with a column operating in the counter-current mode.)

The catalysts used in the process of the present invention are dehydration polycondensation catalysts. Preferred homogeneous polycondensation catalysts are those acids with a pKa less than about 4, preferably with a pKa less than about 2, and include inorganic acids, organic sulfonic acids, heteropolyacids, perfluoroalkyl sulfonic acids and mixtures thereof. Also preferred are metal salts of acids with a pKa less than about 4, including metal sulfonates, metal trifluoroacetates, metal triflates, and mixtures thereof including mixtures of the salts with their conjugate acids. Specific examples of catalysts include sulfuric acid, fluorosulfonic acid, phosphorous acid, p-toluenesulfonic acid, benzenesulfonic acid, phosphotungstic acid, phosphomolybdic acid, trifluoromethanesulfonic acid, 1,1,2,2-tetrafluoroethanesulfonic acid, 1,1,1,2,3,3-hexafluoropropanesulfonic acid, bismuth triflate, yttrium triflate, ytterbium triflate, neodymium triflate, lanthanum triflate, scandium triflate, zirconium triflate. A preferred catalyst is sulfuric acid, used in a concentration of from 0.1 to 5.0%, by weight of the reaction mixture. A preferred concentration range is 0.25 to 2.5%.

Suitable heterogeneous catalysts are zeolites, acid-treated silica, acid-treated silica-alumina, acid-treated clays, heterogeneous heteropolyacids and sulfated zirconia.

Generally, catalyst concentrations are typically about 0.1% or more, by weight of the reaction mixture, more preferably about 0.25% or more, and preferably used in a concentration of about 20% or less, by weight of the reaction mixture, more preferably 10% or less, even more preferably 5% of less, and most preferably 2.5% or less. Catalyst concentrations can be as high as 20 weight % for heterogeneous catalysts and lower than 5 weight % for soluble catalysts.

Catalyst precursors may also be employed. For example, 1,3-dibromo-propane yields, after reaction with 1,3-propanediol, hydrogen bromide which then functions as a dehydration catalyst. Similar results are obtained with 1,3-diiodo-propane and other dihaloalkanes.

The process of the present invention will provide polytrimethylene ether glycol continuously with improvement in polymerization rate and polymer color.

The starting material for the present process can be any 1,3-propanediol reactant or a mixture thereof. The quality of the starting material is important for producing high quality polymer. The 1,3-propanediol employed in the process of the present invention may be obtained by any of the various chemical routes or by biochemical transformation routes. Preferred routes are described in U.S. Pat. Nos. 5,015,789, 5,276,201, 5,284,979, 5,334,778, 5,364,984, 5,364,987, 5,633,362, 5,686,276, 5,821,092, 5,962,745 and 6,140,543, U.S. patent application Ser. Nos. 09/346,418, 09/382,970, 09/382,998 and 09/505,785, and WO 98/57913, 00/10953 and WO 00/14041, all of which are incorporated herein by reference. Preferably the 1,3-propanediol has a purity of greater than 99%. The 1,3-propanediol-based starting materials may be purified prior to use, for example by treatment with an acid catalyst at an elevated temperature and reaction time to react impurities into forms that can be separated as described in WO 00/10953, which is incorporated herein by reference.

In some instance, it may be desirable to use up to 10% or more of low molecular weight oligomers where they are available. Thus, preferably the starting material consists essentially of 1,3-propanediol diol and dimer and trimer thereof. The most preferred starting material is comprised of 90 weight % or more 1,3-propanediol, more preferably 99 weight % or more.

The starting material for the present process can contain up to 50% by weight (preferably 20 weight % or less) of comonomer diols in addition to the 1,3-propanediol and/or its oligomers. Comonomer diols that are suitable for use in the process include aliphatic diols, for example 1,6-hexanediol, 1,7-heptanediol, 1,8-octanediol, 1,9-nonanediol, 1,10-decanediol, 1,12-dodecanediol, 3,3,4,4,5,5-hexafluro-1,5-pentanediol, 2,2,3,3,4,4,5,5-octafluoro-1,6-hexanediol, 3,3,4,4,5,5,6,6,7,7,8,8,9,9,10,10-hexadecafluoro-1,12-dodecanediol, cycloaliphatic diols, for example 1,4-cyclohexanediol, 1,4-cyclohexanedimethanol and isosorbide, polyhydroxy compounds, for example glycerol, trimethylolpropane, and pentaerythritol. A preferred group of comonomer diol is selected from the group consisting of 2-methyl-1,3-propanediol, 2,2-dimethyl-1,3-propanediol, 2,2-diethyl-1,3-propanediol, 2-ethyl-2-(hydroxymethyl)-1,3-propanediol, 1,6-hexanediol, 1,8-octanediol, 1,10-decanediol, isosorbide, and mixtures thereof. Thermal stabilizers, antioxidants and coloring materials may be added to the polymerization mixture or to the final polymer if necessary.

There is also provided in this invention a continuous process comprising a continuous multi-stage process comprising in an upflow column reactor, providing as reactant or product a liquid phase and a gas or vapor phase to the reactor wherein the gas or vapor phase is continuously removed at the top and at least one intermediate stage. Preferably the process is a condensation process wherein the process forms a gas or vaporous product by condensing one or more of the reactants. An example of such a reaction is a dehydration reaction wherein water vapor is generated, for example in the reactant of 1,3-propanediol to produce polytrimethylene ether glycol and water.

The process of this invention provides a high purity, high molecular weight polymer of polytrimethylene ether glycol having a number average molecular weight of at least 1,000, more preferably at least 1,500, even more preferably at least 1,650 and most preferably at least 2,000. Similarly the molecular weight is less than 5,000 (e.g., 4,950 or less), preferably less than 4,000, and more preferably less than 3,500. The polymer after purification has essentially no acid end groups. For a polymer having a number average molecular weight of 2,350, the hydroxyl number (ASTM E222 method) is 47.5.

Advantageously, the polymer has an APHA (prior to any post purification) (ASTM D1209) color of less than 120, preferably less than 100 and more preferably less than 50. There is also an OCE (oligomers of cyclic ethers) content (prior to any post purification) of less than 2%, preferably less than 1%.

The polyether glycol prepared by the process of the present invention can be purified further to remove the acid present by means known in the art. It should be recognized that in certain applications the product may be used without further purification. However, the purification process improves the polymer quality and functionality significantly and it is comprised of (1) a hydrolysis step to hydrolyze the acid esters that are formed during the polymerization and (2) typically (a) water extraction steps to remove the acid, unreacted monomer, low molecular weight linear oligomers and oligomers of cyclic ethers (OCE), (b) a solid base treatment to neutralize the residual acid present and (c) drying and filtration of the polymer to remove the residual water and solids.

The invention is a low cost, rate efficient continuous way to produce 3G polyol or improved quality. It is particularly advantageous for producing 3G polyol with a desired molecular weight and low color.

The invention is demonstrated in the following examples, which are not intended to be limiting, wherein all parts, percentages and the like are by weight, unless indicated otherwise.

EXAMPLES

Example 1

Dehydration of 1,3-propanediol in a Single Stage Column

In this example the flow-through reactive column used was a single stage Vigreux distilling glass column with a column length of 600 mm and 24/40 ground glass joints. It was obtained from Lab Glass Inc., Vineland, N.J. (Model No. LG-5890).

The glass column reactor sets atop a round-bottom flask and was equipped with a distillation head with a Liebig take-off condenser which was cooled by running water at ambient temperature. The condenser was fitted with a graduated fraction cutter and a distillate receiver. The Vigreux column was heated by wrapping with heater tape; it was insulated and maintained at 200° C. and above. A hot oil condenser maintained at 110° C. was utilized at between the top of the column and the distillation head to condense and recycle back any 3G vaporized in the column during the polymerization.

3G monomer with dissolved catalyst was introduced at the top of the Vigreux column, through a liquid injection pump, such as ISCO LC-5000 syringe pump, (ISCO, Inc., Lincoln, Nebr.) having a range of injection rate between 1.5 to 400 mL per hour. The polymerization took place in the multi-manifolds of the column, which was maintained at elevated temperature, in this example 200° C. and above. Regulated nitrogen was introduced in the bottom of the column. (Estimated rate: 25 ml/minute) The 3G polyol polymer product of the reaction was collected in the round-bottom flask which was optionally immersed in a water bath for temperature control.

The first example of continuous 3G polyol polymerization in the bench scale glass reactive column pilot reactor (run 1) demonstrated the control of the reactor stability and that dehydration of the monomer via etherification occurred with minimum degradation. The residence time in this single stage column (with essentially plug flow) was 45 seconds. At 1.3 ml/minute injection rate at 200° C., with 1% sulfuric acid as catalysts, a 2% yield was obtained, based on the amount of water condensate collected. The condensate was almost pure water (as demonstrated by refractive index) and the color of both the water condensate and the product liquid was water clear.

The results of run 1 and runs 2–4 at higher temperatures and/or longer retention times are shown in Table 1. Increasing the apparent column temperature from 200 to 220° C. (actual reaction temperature: from 190 to 210° C.), led to a 300+% improvement in calculated yield. The calculated yield, based on the amount of water condensate, increased from 2.1% to 7.1%. The condensate was again essentially pure water. Both the condensate and the polymer liquid were water clear. There were no signs of degradation. The apparent activation energy for the polycondensation was estimated to be about 20 KCal/mole.

TABLE 1

3G Continuous Polymerization in a Vigreux Column

| Run Number | Feed Material | Feed Rate (mL/min) | Column Temp. (° C.) | Condensate Mass (g) | R.I.* | Yield | Residence Time (min) |
|---|---|---|---|---|---|---|---|
| 1 | 3G + H$_2$SO$_4$ (1%) | 1.24 | 200 | 0.90 | 1.3400 | 2.1% | 0.75 |
| 2 | 3G + H$_2$SO$_4$ (1%) | 1.20 | 212 | 2.21 | 1.3397 | 6.0% | 1.13 |
| 3 | 3G + H$_2$SO$_4$ (1%) | 1.08 | 217 | 2.60 | 1.3394 | 8.0% | 1.00 |
| 4 | 3G + H$_2$SO$_4$ (1%) | 0.99 | 216 | 3.24 | 1.3423 | 10.9% | 1.17 |

*R.I. is the refractive index of the condensate at 25° C. The R.I. of water is 1.3327 at 25° C.

Example 2

Dehydration of 1,3-propanediol in a Glass Bead Packed Column

The column of Example 1 was modified to increase the number of stages and to lengthen the residence time (and mixing) and to increase the yield. This example demonstrated the 3G continuous polymerization in a glass column reactor similar to that of Example 1, except that a single stage conventional distillation column packed with glass beads was used instead of the Vigreux column.

The column used in this example was a Hempel type distillation column of 500 mm in length and with 24/40 ground glass joints. (Lab Glass Inc, Vineland, N.J., Model No. LG-5820.) It is plain tube with a sealed-in glass honeycomb support for packing near the bottom. The column was packed with glass beads of 5 mm diameter (Lab Glass Inc., Model No. LG-6750-104).

In all other respects, the polymerization reactor was identical to that in Example 1. The residence time of 3G in the column under these conditions was about 1.5 minutes. Results of the 3G continuous polymerization are summarized in Table 2. As in Example 1, yield was calculated from the amount of water condensate collected. Characterization of the product from run 6 is included in Table 6.

TABLE 2

3G Continuous Polymerization in a Glass Bead Packed Column

| Run | Feed Material | Feed Rate (mL/min) | Column Temp. (° C.) | Condensate Mass (g) | R.I.[a] | Yield | Residence Time (min) |
|---|---|---|---|---|---|---|---|
| 5 | 3G + $H_2SO_4$ (1%) | 1.32 | 200 | 6.43 | 1.3365 | 16.2% | 1.42 |
| 6 | 3G + $H_2SO_4$ (1%) | 1.32 | 208 | 10.10 | 1.3383 | 25.5% | 1.25 |
| 7 | 3G + $H_2SO_4$ (1%) | 1.20 | 219 | 7.71 | 1.3395 | 21.4% | 1.72 |
| 8 | 3G + $H_2SO_4$ (1%) | 1.13 | 214 | 7.16 | 1.3388 | 21.1% | 1.72 |
| 9 | 3G + $H_2SO_4$ (1%) | 1.13 | 208 | 7.00 | 1.3385 | 20.7% | 1.93 |

[a]R.I. is the refractive index of the condensate at 25° C. The R.I. of water is 1.3327 at 25° C.

Example 3

Dehydration of 1,3-propanediol in a Single Stage Glass Bead Packed Column with Multiple Passes The conditions of Example 2 (bead packed column) were repeated to simulate a multi staged reactor. After a complete passing of the reaction mixture through the column as in Example 2, the collected effluent from the round bottom flask was passed through the column repeatedly. Run number 10 was thus a single pass experiment similar to runs 5–9 above. Run number 11 uses the product of run 10 as feed material. Run number 14 below, then, was the result of 5 passes through the single pass column simulating a 5 stage reactor. Yield was calculated from the amount of water condensate collected. Characterization of the products from run numbers 12, 13 and 14 is included in Table 6.

TABLE 4

3G Polyol Continuous Polymerization - Single Stage Column/Multi-Pass Experiment[a]

| Polymerization Run Number | Feed Material | Feed Rate (mL/min) | Column Temp (° C.) | Condensate Mass (g) | Accumulative Yield | Residence Time (min) |
|---|---|---|---|---|---|---|
| 10 | 3G + $H_2SO_4$ (1%) | 1.07 | 210 | 4.36 | 10.9% | 1.63 |
| 11 | Run 10 Product | 1.06 | 211 | 5.07 | 23.5% | 1.33 |
| 12 | Run 11 Product | 1.12 | 210 | 4.98 | 35.9% | 1.53 |
| 13 | Run 12 Product | 1.08 | 212 | 4.60 | 47.4% | 1.40 |
| 14 | Run 13 Product | 0.99 | 216 | 1.87 | 52.0% | 1.28 |

[a]The single stage column used is the glass bead packed column as described in Example 2

Example 4

Dehydration of 1,3-propanediol in a Multi Stage Column

The apparatus of example 1 was modified. The Vigreaux column was replaced with a an Oldershaw perforated bubble plate distilling column with 20 stages. (Model no. LG-5621, Lab Glass Inc., Vineland, N.J.). Conditions for runs number 15–18 are presented in Table 5. Yield was calculated from the amount of water condensate collected. Characterization of the product from run number 15 is included in Table 6. Table 7, below compares the results of two batch experiments, not of the invention, to continuous runs number 15, 17 and 18.

TABLE 5

3G Polyol Continuous Polymerization-Multi-Stage Column Experiment[a]

| Polymerization Run Number | Feed Material | Feed Rate (mL/min) | Set Temp. (° C.) | Condensate Mass (g) | Yield | Residence Time (min) |
|---|---|---|---|---|---|---|
| 15 | 3G + H$_2$SO$_4$ (1%) | 1.12 | 210 | 15.66 | 46.9% | 12.00 |
| 16 | 3G + H$_2$SO$_4$ (1%) | 0.98 | 210 | 18.37 | 63.0% | 12.45 |
| 17 | 3G + H$_2$SO$_4$ (2.5%) | 1.06 | 210 | 30.37 | 96.3% | 11.13 |
| 18 | 3G + H$_2$SO$_4$ (4.0%) | 1.06 | 210 | 37.98 | 109% | 10.00 |

TABLE 6

Molecular Weight[a] of 3G Polyol Produced from Continuous Polymerization in a Column Reactor

| Oligomer | n | MW$_i$ g/mol | Sample - Run #6 n$_i$ (%)[b] | n$_i$ * MW$_i$ | Sample - Run #12 n$_i$ (%)[b] | n$_i$ * MW$_i$ | Sample - Run #13 n$_i$ (%)[b] | n$_i$ * MW$_i$ | Sample - Run #14 n$_i$ (%)[b] | n$_i$ * MW$_i$ | Sample - Run #15 n$_i$ (%)[b] | n$_i$ * MW$_i$ |
|---|---|---|---|---|---|---|---|---|---|---|---|---|
| 3G | — | 76.095 | 60.600 | 46.114 | 42.000 | 31.960 | 23.900 | 18.187 | 15.200 | 11.566 | 27.800 | 21.154 |
| Dimer | 2 | 134.175 | 17.400 | 23.346 | 25.500 | 34.215 | 24.400 | 32.739 | 22.000 | 29.519 | 24.000 | 32.202 |
| Trimer | 3 | 192.255 | 4.440 | 8.536 | 10.200 | 19.610 | 14.100 | 27.108 | 15.200 | 29.223 | 12.800 | 24.609 |
| Tetramer | 4 | 250.335 | 1.790 | 4.481 | 4.160 | 10.414 | 7.960 | 19.927 | 9.500 | 23.782 | 6.610 | 16.547 |
| Pentamer | 5 | 308.415 | 0.724 | 2.233 | 1.660 | 5.120 | 4.060 | 12.522 | 5.200 | 16.038 | 3.240 | 9.993 |
| Hexamer | 6 | 366.495 | 0.401 | 1.470 | 0.752 | 2.756 | 1.990 | 7.293 | 2.910 | 10.665 | 1.720 | 6.304 |
| Heptamer | 7 | 424.575 | 0.320 | 1.359 | 0.393 | 1.669 | 1.070 | 4.543 | 1.580 | 6.708 | 1.110 | 4.713 |
| Octamer | 8 | 482.655 | 0.150 | 0.724 | 0.160 | 0.772 | 0.410 | 1.979 | 0.700 | 3.379 | 0.500 | 2.413 |
| Sum w/o 3G | | | 25.225 | 42.149 | 42.825 | 74.555 | 53.990 | 106.110 | 57.090 | 119.313 | 49.980 | 117.935 |
| Sum w/ 3G | | | 85.825 | 88.262 | 84.825 | 106.515 | 77.890 | 124.297 | 72.290 | 130.879 | 77.780 | |
| Mn w/o 3G (g/mol) | | | | 167.091 | | 174.093 | | 196.537 | | 208.990 | | 193.638 |
| Mn w/ 3G (g/mol) | | | | 102.840 | | 125.570 | | 159.580 | | 181.047 | | 151.626 |

TABLE 7

3G Polyol Polymerization Batch vs. Continuous Column Process

| Polymerization | Catalyst[a] Percentage | Residence Time (min) | Polymer Viscosity (cPoise) | Polymer Molecular Wt. (Mn) |
|---|---|---|---|---|
| Batch experiment a | 1.0% | 240.00 | 226.3 | 417[a] |
| Batch experiment b | 1.0% | 240.00 | 352.3 | 680[a] |
| Continuous (Run no. 15) | 1.0% | 12.00 | 79.4 | 193.6[b], 179[a] |
| Continuous (Run no. 17) | 2.5% | 11.13 | 341.0 | 500[a] |
| Continuous (Run no. 18) | 4.0% | 10.00 | 599.3 | 690[a] |

[a]from Nuclear Magnetic Resonance analysis
[b]from Gas Chromatography analysis

Example 5

1,3-Propanediol was mixed with sufficient sulfuric acid to provide a 10% solution of the acid in the diol. This solution was transferred to a mixing drum and diluted with the diol to provide a 1% solution of sulfuric acid in the diol. The solution was preheated to a temperature of 120° C.

The preheated 1% sulfuric acid/diol solution was introduced to the bottom of a co-current upflow 15-stage continuous glass column reactor, equipped with a central heating unit, wherein the stages were separated by perforated flow distribution plates (trays). Nitrogen was introduced at a low flow rate at the bottom of the column to provide initial agitation.

Polymer product was discharged from the side of the column reactor near the top, and collected. Water and water vapor were swept from the top of the column, condensed, and collected. Results are presented below in Table 8 for several runs, 1–4, under these conditions.

Example 6

Example 5 was repeated except that the column was divided into 8 reaction stage, with the temperature in stages 1 and 2 at 175° C., temperature in stages 3–5 was 190° C., and temperature in stages 6–8 was 180° C. The polymer production rate was 0.8 kg/hr. Vacuum was applied and the absolute pressure was 100 mm Hg. In the final stage, there was a sweep of nitrogen provided at a rate of 0.4 kg/hr, which reduced the steam partial pressure in stage 8 to 33 mm Hg. Results are included as Run 5 in Table 8.

Example 7

Example 6 was repeated but with steam being substantially all withdrawn at the top of stage 4 and nitrogen being added at the bottom of stage 5 at a rate of 0.4 kilograms per hour. The temperature of all stages was held at around 180° C. Absolute pressure at the top of the reactor was 100 mm Hg. Polymer production rate was 0.8 kg/hour. Results are included as Run 6 in Table 8.

Example 8

Example 7 was repeated but with the temperature of the top 4 stages increased to 190° C. Results are included as Run 7 in Table 8.

TABLE 8

3G Polyol Continuous Polymerization - Multi-Stage Column/Co-current Upflow

| Polymerization Run Number | Acid Concentration | Polymer Rate (kg/hr) | Column Temp (° C.) | Number Average MW of polymer |
|---|---|---|---|---|
| 1 | 1% $H_2SO_4$ | 3.82 | 180 | 252 |
| 2 | 1% $H_2SO_4$ | 3.05 | 180 | 546 |
| 3 | 1% $H_2SO_4$ | 2.29 | 180 | 792 |
| 4 | 1% $H_2SO_4$ | 3.82 | 190 | 852 |
| 5 | 1% $H_2SO_4$ | 0.8 | 175, 190, 180 | 1680 |
| 6 | 1% $H_2SO_4$ | 0.8 | 180 | 1801 |
| 7 | 1% $H_2SO_4$ | 0.8 | 180, 180, 190 | 1898 |

As can be seen from Table 8, a range of molecular weights can be by varying reaction conditions.

The run 5 polymer was purified as described below. Equal volume of water was added to the polymer and the reaction mixture was maintained at 100° C. for 6 hours and a stirring speed of 180 rpm under a nitrogen atmosphere. After 6 hours, the heater and the stirrer were turned off and the mixture was allowed to phase separate. The top aqueous phase was decanted and the polyether phase was washed further with distilled water three more times to extract out most of the acid and the oligomers. The residual acid left in the polyether glycol was neutralized with calcium hydroxide in excess. The polymer was dried at 100° C. under reduced pressure for 2–3 hours and then the dried polymer was filtered hot through a Whatman filter paper precoated with a Celite filter aid. The number average molecular weight determined from NMR was found to be 2,140.

The foregoing disclosure of embodiments of the present invention has been presented for purposes of illustration and description. It is not intended to be exhaustive or to limit the invention to the precise forms disclosed. Many variations and modifications of the embodiments described herein will be evident to one of ordinary skill in the art in light of the above disclosure.

The invention claimed is:

1. A continuous process of making polytrimethylene ether glycol comprising:
   (a) continuously providing 1,3-propanediol reactant and polycondensation catalyst; and
   (b) continuously polycondensing the 1,3-propanediol reactant to polytrimethylene ether glycol in a column reactor having two or more reaction stages using the polycondensation catalyst.

2. The process of claim 1 wherein the catalyst is homogeneous.

3. The process of claim 2 wherein the catalyst is selected from the group consisting of a Lewis Acid, a Bronsted Acid, a super acid, and mixtures thereof.

4. The process of claim 3 wherein the catalyst is selected from the group consisting of inorganic acids, organic sulfonic acids, heteropolyacids, and metal salts thereof.

5. The process of claim 1 wherein the catalyst is selected from the group consisting of sulfuric acid, fluorosulfonic acid, phosphorus acid, p-toluenesulfonic, benzenesulfonic acid, phosphotungstic acid, phosphomolybdic acid, trifluoromethanesulfonic acid, 1,1,2,2-tetrafluoro-ethanesulfonic acid, 1,1,1,2,3,3-hexafluoropropanesulfonic acid, bismuth triflate, yttrium triflate, ytterbium triflate, neodymium triflate, lanthanum triflate, scandium triflate and zirconium triflate.

6. The process of claim 1 wherein the catalyst is sulfuric acid.

7. A continuous multi-stage process comprising reacting at least one reactant in a liquid phase in an up-flow column reactor having two or more stages, and forming a gas or vapor phase by-product wherein the gas or vapor phase by-product is continuously removed at the top and at least one intermediate stage.

8. The process of claim 1 wherein the polycondensing is carried out at a temperature greater than 150° C.

9. The process of claim 8 wherein the temperature is greater than 160° C.

10. The process of claim 8 wherein the temperature is greater than 180° C.

11. The process of claim 1 wherein the polycondensing is carried out at a temperature less than 250° C.

12. The process of claim 11 wherein the temperature is less than 220° C.

13. The process of claim 11 wherein the temperature is less than 210° C.

14. The process of claim 8 wherein the temperature is less than 210° C.

15. The process of claim 1 wherein the polycondensation is carried out at a pressure of less than one atmosphere.

16. The process of claim 15 wherein the pressure is less than 500 mm Hg.

17. The process of claim 15 wherein the pressure is less than 250 mm Hg.

18. The process of claim 15 wherein the pressure is greater than 1 mm Hg.

19. The process of claim 18 wherein the pressure is greater than 20 mm Hg.

20. The process of claim 18 wherein the pressure is greater than 50 mm Hg.

21. The process of claim 1 wherein the 1,3-propanediol reactant is selected from: 1,3-propanediol dimers of 1,3-propanediol, trimers of 1,3-propanediol, and mixtures thereof.

22. The process of claim 21 wherein the 1,3-propanediol reactant is selected from: 1,3-propanediol, and a mixture containing at least 90 weight % of 1,3-propanediol.

23. The process of claim 21 wherein the 1,3-propanediol reactant is 1,3-propanediol.

24. The process of claim 23 wherein the polycondensation pressure is between 50 and 250 mm Hg.

25. The process of claim 1 wherein the column reactor is equipped with a heat source located within the reaction medium.

26. The process of claim 1, wherein the column reactor has 3–30 stages.

27. The process of claim 1 wherein the column reactor is a vertical column reactor and has 4–20 stages.

28. The process of claim 1 wherein the column reactor has 8–15 stages.

29. The process of claim 1 wherein the 1,3-propanediol reactant is fed at multiple locations to the reactor.

30. The process 1 wherein an inert gas is added to the reactor at one or more stages.

31. The process of claim 1 wherein water vapor is generated as a by-product of the reaction and is removed from the reactor in at least one intermediate stage.

32. A continuous process of making polytrimethylene ether glycol comprising:
(a) providing 1,3-propanediol reactant,
(b) providing polycondensation catalyst; and
(b) polycondensing the 1,3-propanediol reactant to polytrimethylene ether glycol;
wherein the polycondensation is first carried out in at least one prepolymerizer reactor and then polycondensation continued continuously in a column reactor having two or more reaction stages using the polycondensation catalyst, the 1,3-propanediol reactant comprises 90 weight % or more 1,3-propenediol, and in the prepolymerizer reactor the 1,3-propanediol is polymerized with the polycondensation catalyst to a degree of polymerization of at least 5.

33. The process of claim 32 wherein the 1,3-propanediol reactant is 1,3-propanediol and in the at least one prepolymerizer reactor the 1,3-propanediol is polymerized with the catalyst to a degree of polymerization of at least 20.

34. The process of claim 33 wherein the at least one prepolymerizer reactor is a well-mixed tank reactor.

35. The process of claim 33 wherein steam generated in the at least one prepolymerizer reactor is removed and the product of the at least one prepolymerizer is fed to the column reactor.

36. The process of claim 33 wherein an inert gas is fed to the column reactor.

37. The process of claim 1 wherein the polytrimethylene ether glycol has a number average molecular weight of at least 1,000.

38. The process of claim 1 wherein the 1,3-propanediol reactant comprises 20 weight percent or less of one or more comonomer diols.

39. The process of claim 38 wherein said comonomer diols are selected from: 1,6-hexanediol, 1,7-heptanediol, 1,8-octanediol, 1,9-nonanediol, 1,10-decanediol, 1,12-dodecanediol, 3,3,4,4,5,5-hexafluoro-1,5-pentanediol, 2,2,3,3,4,4,5,5-octafluoro-1,6-hexanediol, and 3,3,4,4,5,5,6,6,7,7,8,8,9,9,10,10-hexadecafluoro-1,12-dodecanediol.

40. The process of claim 38 wherein said comonomer diols are selected from cycloaliphatic diols and polyhydroxy compounds.

41. The process of claim 40 wherein said comonomer diols are selected from 1,4-cyclohexanediol, 1,4-cyclohexanedimethanol, isosorbide, glycerol, trimethylolpropane, and pentaerythritol.

42. A continuous process of making polytrimethylene ether glycol comprising: (a) continuously providing 1,3-propanediol reactant and polycondensation catalyst: and (b) continuously polycondensing a 1,3-propanediol reactant to polytrimethylene ether glycol in a reactor at a pressure of less than one atmosphere using the polycondensation catalyst.

43. The process of claim 42 wherein the pressure is less than 500 mm Hg.

44. The process of claim 42 wherein the pressure is less than 250 mm Hg.

45. The process of claim 42 wherein the pressure is greater than 1 mm Hg.

46. The process of claim 45 wherein the pressure is greater than 20 mm Hg.

47. The process of claim 45 wherein the pressure is greater than 50 mm Hg.

48. The process of claim 42 wherein the 1,3-propanediol reactant comprises 20 weight percent or less of one or more comonomer diols.

49. The process of claim 48 wherein said comonomer diols are selected from: 1,6-hexanediol, 1,7-heptanediol, 1,8-octanediol, 1,9-nonanediol, 1,10-decanediol, 1,12-dodecanediol, 3,3,4,4,5,5-hexafluoro-1,5-pentanediol, 2,2,3,3,4,4,5,5-octafluoro-1,6-hexanediol, and 3,3,4,4,5,5,6,6,7,7,8,8,9,9,10,10-hexadecafluoro-1,12-dodecanediol.

50. The process of claim 48 wherein said comonomer diols are selected from cycloaliphatic diols and polyhydroxy compounds.

51. The process of claim 50 wherein said comonomer diols are selected from 1,4-cyclohexanediol, 1,4-cyclohexanedimethanol, isosorbide, glycerol, trimethylolpropane, and pentaerythritol.

52. The process of claim 42 wherein the 1,3-propanediol reactant is selected from: 1,3-propanediol, dimers of 1,3-propanediol, trimers of 1,3-propanediol, and mixtures thereof.

53. The process of claim 42 wherein the 1,3-propanediol reactant is selected from; 1,3-propanediol, and a mixture containing at least 90 weight % of 1,3-propanediol.

54. The process of claim 42 wherein the 1,3-propanediol reactant is 1,3-propanediol.

55. A continuous process of making polytrimethylene ether glycol comprising: continuously providing (1) 1,3-propanediol reactant selected from the group consisting of 1,3-propanediol and/or oligomers or prepolymers of 1,3-propanediol having a degree of polymerization of 2–9 and mixtures thereof, (2) 20 weight % or less of comonomer diol, and (3) polycondensation catalyst; and continuously polycondensing the 1,3-propanediol reactant and the 20 weight % or less of comonomer diol to form polytrimethylene ether glycol in a column reactor having two or more reaction stages using the polycondensation catalyst.

56. A continuous process of making polytrimethylene ether glycol comprising:
 a. providing 1,3-propanediol reactant selected from the group consisting of 1,3-propanediol and/or dimer and trimer of 1,3-propanediol and mixtures thereof,
 b. optionally providing 20 weight % or less of comonomer diol;
 c. providing polycondensation catalyst; and
 d. polycondensing the 1,3-propanediol reactant and any optional comonomer diol to polytrimethylene ether glycol;
wherein the polycondensation is first carried out in at least one prepolymerizer reactor and then polycondensation continued continuously in a column reactor having two or more reaction stages using the polycondensation catalyst, the 1,3-propanediol reactant comprises 90 weight % or more 1,3-propenediol, and in the prepolymerizer reactor the 1,3-propanediol and any optional comonomer diol is polymerized with the polycondensation catalyst to a degree of polymerization of at least 5.

57. A continuous process of making polytrimethylene ether glycol comprising: (a) continuously providing (1) 1,3-propanediol reactant selected from the group consisting of 1,3-propanediol and/or oligomers or prepolymers of 1,3-propanediol having a degree of polymerization of 2–9 and mixtures thereof, (2) 20 weight % or less of comonomer diol, and (3) polycondensation catalyst; and (b) continuously polycondensing the 1,3-propanediol reactant and the 20 weight % or less of comonomer diol to form polytrimethylene ether glycol in a reactor at a pressure of less than one atmosphere using the polycondensation catalyst.

* * * * *